United States Patent [19]

Maurer et al.

[11] 4,423,058
[45] Dec. 27, 1983

[54] COMBATING PESTS WITH NOVEL PYRAZOL-4-YL N-ALKYLCARBAMATES

[75] Inventors: Fritz Maurer, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 360,138

[22] Filed: Mar. 22, 1982

[30] Foreign Application Priority Data

Apr. 11, 1981 [DE] Fed. Rep. of Germany ....... 3114833

[51] Int. Cl.³ .................. A01N 435/56; C07D 231/18
[52] U.S. Cl. ............................... 424/273 P; 548/375; 548/377
[58] Field of Search ............................. 548/375, 377; 424/273 P

[56] References Cited

FOREIGN PATENT DOCUMENTS

| 23326 | 2/1981 | European Pat. Off. |
| 1108202 | 6/1961 | Fed. Rep. of Germany |
| 2420360 | 11/1975 | Fed. Rep. of Germany |
| 282655 | 8/1952 | Switzerland |
| 414249 | 12/1966 | Switzerland |

*Primary Examiner*—Robert T. Bond
*Attorney, Agent, or Firm*—Sprung, Horn, Kramer & Woods

[57] ABSTRACT

New pyrazol-4-yl N-alkylcarbamates of the general formula

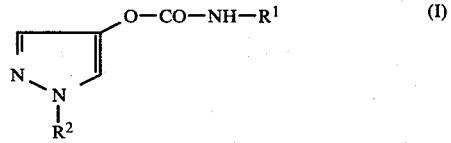

in which
  $R^1$ represents an optionally substituted alkyl group having more than one carbon atom or an alkenyl, alkinyl or cycloalkyl group, and
  $R^2$ represents an optionally substituted alkyl, alkenyl, alkinyl, cycloalkyl, aralkyl or aryl group, can be obtained if a 4-hydroxypyrazole of the general formula

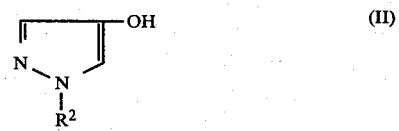

is reacted with an isocyanate of the general formula

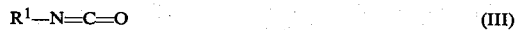

or with a carbamoyl halide of the general formula

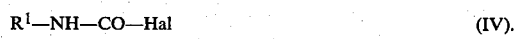

The new compounds are distinguished by a high degree of activity as pest-combating agents, in particular by their insecticidal and nematicidal activity.

9 Claims, No Drawings

COMBATING PESTS WITH NOVEL PYRAZOL-4-YL N-ALKYLCARBAMATES

The invention relates to certain new pyrazol-4-yl N-alkylcarbamates, to several processes for their production and to their use as pest-combating agents, particularly as insecticides and nematicides.

It is known that certain carbamates, such as 1-methyl-pyrazol-4-yl N-methylcarbamate, 1-iso-propyl-pyrazol-4-yl N-methylcarbamate, 1-n-propyl-pyrazol-4-yl N-methylcarbamate and 1-cyclopentyl-pyrazol-4-yl N-methylcarbamate, have pesticidal activity (see U.S. Application Ser. No. 319,767, filed Nov. 9, 1981, now pending).

However, the action of these compounds is not always completely satisfactory, particularly in the case of low active compound concentrations and use quantities.

The present invention now provides, as new compounds, the pyrazol-4-yl N-alkylcarbamates of the general formula

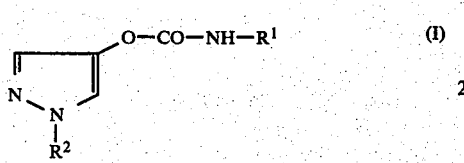

in which
R$^1$ represents an optionally substituted alkyl group having more than one carbon atom or an alkenyl, alkinyl or cycloalkyl group, and
R$^2$ represents an optionally substituted alkyl, alkenyl, alkinyl, cycloalkyl, aralkyl or aryl group.

According to the present invention we further provide a process for the production of a compound of the present invention, characterized in that (a) a 4-hydroxypyrazole of the general formula

in which R$^2$ has the meaning given above, is reacted with an isocyanate of the general formula $$R^1-N=C=O \quad (III)$$

in which R$^1$ has the meaning given above, or (b) a 4-hydroxy-pyrazole of formula (II), as defined in reaction variant (a), is reacted with a carbamoyl halide of the general formula $$R^1-NH-CO-Hal \quad (IV)$$

in which
R$^1$ has the meaning given above and
Hal represents a fluorine or chlorine atom, if appropriate in the presence of a diluent and, if appropriate, in the presence of an acid-binding agent.

The new pyrazol-4-yl N-alkylcarbamates of the present invention are distinguished by a high degree of activity as pest-combating agents, particularly by a high degree of insecticidal and nematicidal activity.

Surprisingly, the compounds according to the present invention exhibit a considerably greater insecticidal and nematicidal action than known compounds of similar constitution and identical direction of action. Their action against insects from the order of the Lepidoptera, such as Heliothis spp., is to be particularly emphasized.

Preferred pyrazol-4-yl N-alkylcarbamates according to the present invention are those in which
R$^1$ represents a straight-chain or branched alkyl group having 2 to 5 carbon atoms, an alkenyl or alkinyl group, each having 3 to 5 carbon atoms or a cycloalkyl group having 2 to 6 carbon atoms, and
R$^2$ represents a straight-chain or branched alkyl group having 1 to 6 carbon atoms, an alkenyl or alkinyl group each having 3 to 5 carbon atoms, a cycloalkyl group having 3 to 6 carbon atoms, an aralkyl group having 6 to 10 carbon atoms in the aryl part and 1 or 2 carbon atoms in the alkyl part, or a phenyl group.

Very particularly preferred pyrazol-4-yl N-alkylcarbamates of the present invention are those in which
R$^1$ represents an ethyl, iso-propyl, n-propyl, n-butyl, iso-butyl, tert.-butyl, 2-methyl-butyl, allyl, propargyl, cyclopropyl, cyclobutyl, cyclopentyl or cyclohexyl group, and
R$^2$ represents a methyl, ethyl, iso-propyl, n-propyl, n-butyl, iso-butyl, tert.-butyl, 1,1-dimethyl-propyl, allyl, propargyl, cyclohexyl, cyclopentyl, cyclobutyl, cyclopropyl, benzyl or phenyl group.

Compounds of the formula (I) in which
R$^1$ represents an ethyl group and
R$^2$ has the meanings given for very particularly preferred compounds of the present invention, are also especially preferred.

Compounds of the formula (I) in which
R$^1$ represents a propyl group and
R$^2$ has the meanings given for very particularly preferred compounds of the present invention are also especially preferred.

Compounds of the formula (I) in which
R$^2$ represents a propyl group and
R$^1$ has the meanings given for very particularly preferred compounds of the present invention and are also especially preferred.

Compounds of the formula (I) in which
R$^2$ represents a butyl group and
R$^1$ has the meanings given for very particularly preferred compounds of the present invention are also especially preferred.

Preferred individual compounds are those compounds mentioned in the preparative examples hereinbelow.

If, for example, 1-iso-propyl-4-hydroxypyrazole and n-propyl isocyanate are used as the starting materials, the course of the reaction variant (a) according to the present invention is illustrated by the following equation:

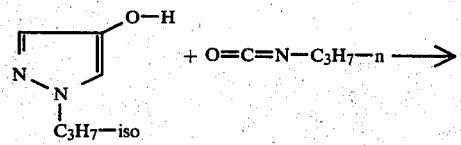

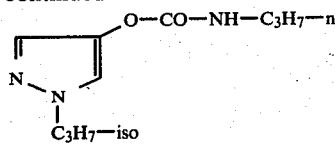

If 1-tert.-butyl-4-hydroxy-pyrazole and N-ethylcarbamoyl fluoride are used as the starting materials, the course of the reaction variant (b) according to the present invention is illustrated by the following equation:

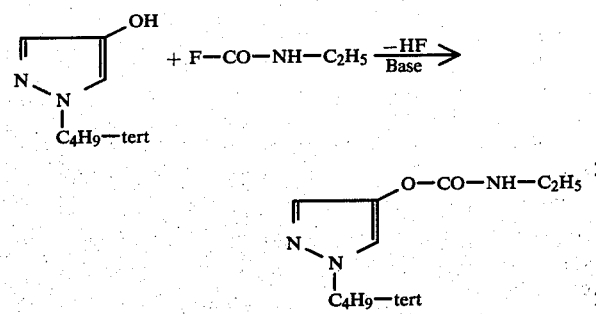

Preferred 4-hydroxy-pyrazoles of formula (II) to be used as starting materials for reaction variants (a) and (b) are those in which $R^2$ represents those radicals which have already been mentioned for this substituent in connection with the description of the preferred and very particularly preferred compounds according to the invention.

The following may be mentioned as examples: 1-methyl-, 1-ethyl-, 1-n-propyl-, 1-iso-propyl-, 1-n-butyl-, 1-iso-butyl-, 1-tert.-butyl-, 1-(1,1-dimethylpropyl)-, 1-allyl-, 1-propargyl-, 1-cyclohexyl-, 1-cyclopentyl-, 1-cyclobutyl-, 1-cyclopropyl-, 1-benzyl-, and 1-phenyl-4-hydroxy-pyrazole.

4-Hydroxy-pyrazoles of the formula (II) are known (see Liebigs Ann. Chemie 313, (1900), 17). They are obtained, for example, by the reaction of known 4-methoxy-pyrazoles with hydrobromic acid. The preparation of the 4-methoxy-pyrazoles is effected, in a known manner, from hydrazine and 2-methoxy-4-dimethylamino-acrolein (see Archiv der Pharmazie 300 (1967), 704–708).

Preferred isocyanates of formula (III) further to be used as starting materials for the reaction variant (a) according to the invention are those in which $R^1$ represents those radicals which have already been mentioned for this substituent in connection with the description of the preferred and very particularly preferred compounds according to the invention.

The following may be mentioned as examples: N-ethyl, N-iso-propyl, N-n-propyl, N-n-butyl, N-iso-butyl, N-tert.-butyl, N-2-methyl-butyl, N-allyl, N-propargyl, N-cyclopropyl, N-cyclobutyl, N-cyclopentyl and N-cyclohexyl isocyanate.

Isocyanates of the formula (III) are known and can be prepared according to generally customary and known processes.

Preferred carbamoyl halides of formula (IV) to be used as starting materials for the reaction variant (b) according to the invention, are those in which $R^1$ represents those radicals which have already been mentioned for this substituent in connection with the description of the preferred and very particularly preferred compounds according to the invention, and Hal represents a fluorine or chlorine atom.

The following may be mentioned as examples: N-ethyl-carbamoyl, N-iso-propyl-carbamoyl, N-n-propyl-carbamoyl, N-n-butyl-carbamoyl, N-iso-butyl-carbamoyl, N-tert.-butyl-carbamoyl, N-2-methylbutyl-carbamoyl, N-allyl-carbamoyl, N-propargyl-carbamoyl, N-cyclopropyl-carbamoyl, N-cyclobutyl-carbamoyl, N-cyclopentyl-carbamoyl and N-cyclohexyl-carbamoyl fluoride or chloride.

The carbamoyl halides of the formula (IV) are known or can be prepared according to generally customary and known processes.

Any of the inert organic solvents are preferred diluents suitable for the reaction variant (a). These include, in particular, aliphatic and aromatic, optionally chlorinated hydrocarbons (such as benzine, benzene, toluene, xylene, methylene chloride, chloroform, carbon tetrachloride, chlorobenzene and o-dichlorobenzene), ethers (such as diethyl ether and dibutyl ether, tetrahydrofuran and dioxane), ketones (such as acetone, methyl ethyl ketone, methyl isopropyl ketone and methyl isobutyl ketone), and nitriles (such as acetonitrile and propionitrile).

The reaction variant (a) is carried out using a catalyst, if appropriate. In particular, aliphatic, aromatic or heterocyclic amines (such as triethylamine, trimethylamine, dimethylaniline, dimethylbenzylamine, pyridine, diazabicyclooctane, diazabicyclononane and diazabicycloundecene) can be used as the catalysts in this process.

The reaction temperature can be varied within a relatively wide range. In general, the reaction is carried out at a temperature between 0° and 100° C., preferably between 10° and 80° C.

The reaction variant (a) is carried out, in general, under normal pressure. In carrying out reaction variant (a) according to the invention, between 1 and 1.5 mols, preferably between 1 and 1.2 mols, of isocyanate of the formula (III) are customarily employed per mol of 4-hydroxypyrazole of the formula (II). The reaction is preferably carried out using one of the abovementioned catalysts in one of the abovementioned diluents. The reaction mixture is stirred for several hours at the required temperature. The solvent is then distilled off in vacuo. The products are thus obtained in an oleaginous or crystalline form. They are characterized by the melting point or the refractive index.

Any of the inert organic solvents are preferred as diluents which are suitable for carrying out the reaction variant (b). These preferably include as preferences the solvents listed for reaction variant (a).

The reaction variant (b) is generally carried out in the presence of acid-binding agents. Any of the inorganic and organic acid-binding agents which can customarily be used can be added. These include, as preferences, alkali metal carbonates (such as sodium carbonate, potassium carbonate and sodium bicarbonate) and lower tertiary alkylamines, cycloalkylamines or arylalkylamines (such as triethylamine and N,N-dimethyl-benzylamine) and furthermore pyridine, 1,4-diazabicyclo[2,2,2]-octane and 1,5-diazabicyclo[4,3,0]-non-5-ene.

The reaction temperature of reaction variant (b) can be varied within a relatively wide range. In general, the reaction is carried out at a temperature between 0° and 100° C., preferably between 10° and 80° C.

The reaction variant (b) is carried out, in general, under normal pressure. In carrying out reaction variant (b) according to the invention, between 1 and 1.5 mols preferably between 1 and 1.2 mols, of carbamoyl halide of the formula (IV) is customarily employed per mol of 4-hydroxy-pyrazole of the formula (II).

The reaction is preferably carried out using one of the abovementioned acid-binding agents in one of the abovementioned diluents. The reaction mixture is stirred for several hours at the required temperature. The solvent is then distilled off in vacuo. The products are thus obtained in an oleaginous or crystalline form. They are characterized by the melting point or the refractive index.

The pyrazol-4-yl N-alkylcarbamates of the present invention are distinguished by outstanding insecticidal and nematicidal activity.

The compounds according to the present invention can be employed, in addition, in combating fungal and bacterial plant diseases.

The active compounds are well tolerated by plants, have a favorable level of toxicity to warm-blooded animals, and are suitable for combating arthropod pests, especially insects, and nematodes, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;*

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects, and nematodes) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

PREPARATIVE EXAMPLES

Example 1

(a) The 4-methoxypyrazoles, some of which are known and which are employed as precursors for the 4-hydroxypyrazoles of formula (II), could be prepared, for example as follows:

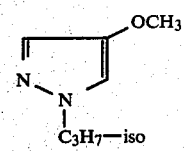

A mixture of 129 g (1 mol) of 2-methoxy-3-dimethylaminoacrolein (for the preparation thereof see Archiv der Pharmazie 300 (1967), pages 704–708), 123 g (1 mol) of isopropylhydrazine hemisulphate and 1.1 ml of a solution of sodium methylate in 400 ml of methanol was boiled under reflux for 24 hours. The solvent was then distilled off in vacuo, 500 ml of water were added to the residue and the mixture was then extracted with 1 liter of chloroform. The organic solution was washed with 500 ml of water, dried over sodium sulphate and then concentrated by evaporation in vacuo at 30° C. The residue was distilled in vacuo and 82.5 g (60% of theory) of 1-isopropyl-4-methoxypyrazole were thus obtained in the form of a yellow oil with a boiling point of 94°–96° C./14 mm Hg.

Other 4-methoxy-pyrazoles were prepared in an analogous manner.

(b) The 4-hydroxy-pyrazoles to be used as starting materials could be prepared, for example, as follows:

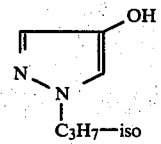

A solution of 27.6 g (0.2 mol) of 1-iso-propyl-4-methoxy-pyrazole in 100 ml of 48% strength hydrobromic acid was boiled under reflux for 9 hours. The excess acid was then distilled off in vacuo, the residue was dissolved in 40 ml of water and the solution was neutralised by the addition of solid sodium bicarbonate. The solution was then extracted with 6×40 ml of chloroform, the combined extracts were dried over sodium sulphate and the solvent was distilled off in vacuo. 18.6 g (75% of theory) of 1-iso-propyl-4-hydroxy-pyrazole remained in the form of beige crystals with a melting point of 63° C.

Other 4-hydroxy-pyrazoles of the formula (II) were prepared in an analogous manner.

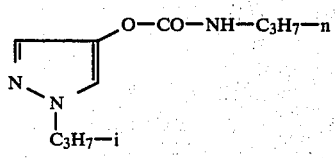

(Reaction varient a)

8.5 g (0.1 mol) of n-propyl isocyanate were added dropwise to a solution of 12.6 g (0.1 mol) of 1-isopropyl-hydroxy-pyrazole and 3 drops of triethylamine in 50 ml of acetone. The reaction mixture was then further stirred for 4 hours at 40° C. and the solvent was distilled off in vacuo. 20 g (95% of theory) of 1-isopropyl-pyrazol-4-yl N-n-propylcarbamate were obtained as a brown oil with a refractive index of $n_D^{22}=1.4885$.

EXAMPLE 2

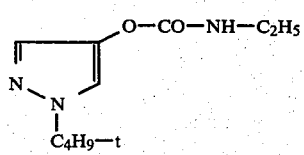

(Reaction varient b)

4.6 g (0.05 mol) of N-ethylcarbamoyl fluoride were added to a mixture of 7 g (0.05 mol) of 1-tert.-butyl-4-hydroxypyrazole, 10.4 g (0.075 mol) of potassium carbonate and 100 ml of acetonitrile. The mixture was stirred for a further 3 hours at 20° C. It was then filtered under suction. The filtrate was concentrated by evaporation in vacuo. 9 g (85% of theory) of 1-tert.-butyl-pyrazol-4-yl N-ethylcarbamate were obtained in the form of beige crystals with a melting point of 77° C.

The compounds of the general formula

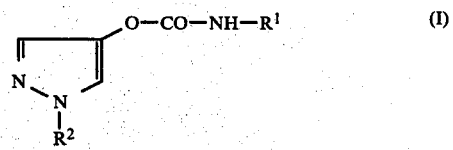

were obtained as described in Examples 1 and 2 and according to the reaction variants (a) and (b):

| Compound No. | R¹ | R² | Physical constants |
|---|---|---|---|
| 3 | C₃H₇—iso | C₃H₇—iso | mp: 54° C. |
| 4 | C₃H₇—iso | C₄H₉—tert | mp: 67° C. |
| 5 | C₂H₅ | C₃H₇—iso | $n_D^{20}$: 1.4904 |
| 6 | C₃H₇—n | C₄H₉—sec. | |
| 7 | C₂H₅ | —C(CH₃)₂—CH₂CH₃ | mp: 93° C. |
| 8 | C₃H₇—n | —C(CH₃)₂—CH₂CH₃ | mp: 71° C. |
| 9 | C₂H₅ | C₃H₇—n | |
| 10 | C₃H₇—iso | —C(CH₃)₂—CH₂CH₃ | |
| 11 | C₂H₅ | C₂H₅ | $n_D^{23}$: 1.4919 |
| 12 | CH₂=CH—CH₂— | C₃H₇—iso | $n_D^{26}$: 1.5018 |
| 13 | CH≡C—CH₂— | C₃H₇—iso | $n_D^{24}$: 1.5059 |
| 14 | ▷— | C₄H₉—tert | mp: 70° C. |
| 15 | ▷— | —C(CH₃)₂—CH₂CH₃ | |
| 16 | CH₂=CH—CH₂— | C₄H₉—tert | mp: 53° C. |
| 17 | CH≡C—CH₂— | C₄H₉—tert | mp: 93° C. |
| 18 | ▷— | C₃H₇—iso | mp: 47° C. |
| 19 | CH₂=CH—CH₂— | —C(CH₃)₂—CH₂CH₃ | |
| 20 | CH≡C—CH₂— | —C(CH₃)₂—CH₂CH₃ | |
| 21 | CH₂=CH—CH₂— | C₄H₉—sec. | |
| 22 | CH≡C—CH₂— | C₄H₉—sec. | |
| 23 | ▷— | C₄H₉—sec. | |
| 24 | CH₂=CH—CH₂— | C₂H₅ | |
| 25 | CH≡C—CH₂— | C₂H₅ | |
| 26 | ▷— | C₂H₅ | |
| 27 | C₂H₅ | ⟨H⟩ | mp: 76° C. |
| 28 | C₂H₅ | C₄H₉sec. | $n_D^{23}$: 1.4882 |

The pesticidal activity of the compounds of this invention is illustrated by the following biotest examples.

In these examples, the compounds according to the present invention are each identified by the number (given in brackets) from Examples 1 and 2 and the table hereinabove.

The known comparison compounds are identified as follows:

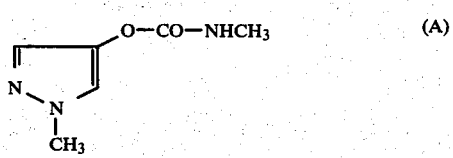

(1-Methyl-pyrazol-4-yl N—methylcarbamate),

-continued

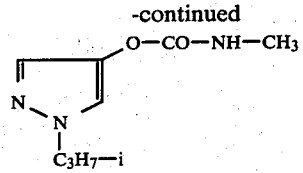

(1-Iso-propyl-pyrazol-4-yl N—methylcarbamate),     (B)

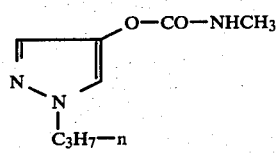

(1-n-Propyl-pyrazol-4-yl N—methylcarbamate), and     (C)

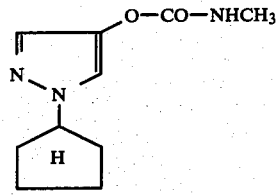

(1-Cyclopentyl-pyrazol-4-yl N—methylcarbamate).     (D)

EXAMPLE 3

*Phaedon larvae* test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the destruction in % was determined. 100% meant that all the beetle larvae had been killed; 0% meant that none of the beetle larvae had been killed.

In this test, for example, the following compounds showed a superior activity compared to the prior art: (1), (2), (4) and (5).

EXAMPLE 4

*Heliothis virescens* test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Soy bean shoots (*Glycine max*) were treated by being dipped into the preparation of the active compound of the desired concentration and were infested with tobacco budworm (*Heliothis virescens*), as long as the leaves were still wet.

After the specified periods of time, the destruction in % was determined. 100% meant that all the worms had been killed; 0% meant that none of the worms had been killed.

In this test, for example, the following compounds showed a superior activity compared to the prior art: (1), (2) and (5).

EXAMPLE 5

Critical concentration test/soil insects
Test insect: *Phorbia antiqua* grubs (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The soil was filled into pots and the pots were left to stand at room temperature.

After 24 hours, the test insects were introduced into the treated soil, and after a further 2 to 7 days the degree of effectiveness of the active compound was determined in % by counting the dead and live test insects. The degree of effectiveness was 100% if all the test insects had been killed and was 0% if just as many test insects were still alive as in the case of the untreated control.

In this test, for example, the following compounds showed a superior action compared to the prior art: (2), (4) and (5).

EXAMPLE 6

Critical concentration test/root-systemic action
Test insect: *Phaeodon cochleariae* larvae
Solvnet: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, which was given in ppm (=mg/l) being decisive. The treated soil was filled into pots and these were planted with cabbage (Brassica oleracea). The active compound could in this way be taken up from the soil by the roots of the plants and be transported into the leaves.

To demonstrate the root-systemic effect, exclusively the leaves were infested with the abovementioned test larvae after 7 days. After a further 2 days, the evaluation was made by counting or estimating the dead animals. The root-systemic action of the active compound was deduced from the mortality figures. It was 100% it all the test larvae had been killed and 0% if just as many test insects were still alive as in the case of the untreated control.

In this test, for example, the following compounds showed a superior action compared to the prior art: (1), (2), (4) and (5).

EXAMPLE 7

Critical concentration test/nematodes
Test nematode: Meloidogyne incognita
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance, only the amount of active compound per unit volume of soil, which was given in ppm, being decisive. The treated soil was filled into pots, lettuce was sown in and the pots were kept at a greenhouse temperature of 27° C.

After four weeks, the lettuce roots were examined for infestation with nematodes (root galls), and the degree of effectiveness of the active compound was determined in %. The degree of effectiveness was 100% if infestation was completely avaoided and was 0% if the infestation was just as high as in the case of the control plants in untreated soil which has been infested in the same manner.

In this test, for example, the following compounds showed a superior activity compared to the prior art: (2) and (4).

It will be understood that the specification and examples are illustrative but not limitative of the present invention and that other embodiments within the spirit and scope of the invention will suggest themselves to those skilled in the art.

We claim:

1. A 1-substituted-pyrazol-4-yl N-alkylcarbamate of the formula

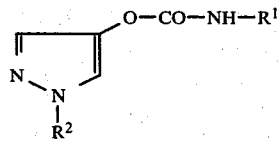

in which
R$^1$ is an alkyl group having 2 to 5 carbon atoms, an alkenyl or alkinyl group, each having 3 to 5 carbon atoms or a cycloalkyl group having 3 to 6 carbon atoms, and
R$^2$ is an alkyl group having 1 to 6 carbon atoms, an alkenyl or alkinyl group, each having 3 to 5 carbon atoms, a cycloalkyl group having 3 to 6 carbon atoms, an aralkyl group having 6 to 10 carbon atoms in the aryl part and 1 or 2 carbon atoms in the alkyl part, or a phenyl group.

2. A compound according to claim 1, in which
R$^1$ is an ethyl, iso-propyl, n-propyl, n-butyl, iso-butyl, tert.-butyl, 2-methyl-butyl, allyl, propargyl, cyclopropyl, cyclobutyl, cyclopentyl or cyclohexyl group, and
R$^2$ is a methyl, ethyl, iso-propyl, n-propyl, n-butyl, iso-butyl, tert.-butyl, 1,1-dimethylpropyl, allyl, propargyl, cyclohexyl, cyclopentyl, cyclobutyl, cyclopropyl, benzyl or phenyl group.

3. A compound according to claim 1, wherein such compound is 1-isopropyl-pyrazol-4-yl N-n-propylcarbamate of the formula

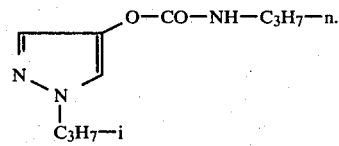

4. A compound according to claim 1, wherein such compound is 1-tert.-butyl-pyrazol-4-yl N-ethylcarbamate of the formula

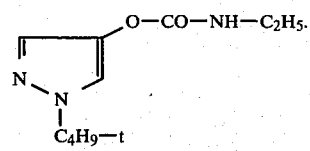

5. A compound according to claim 1, wherein such compound is 1-tert.-butyl-pyrazol-4-yl N-isopropylcarbamate of the formula

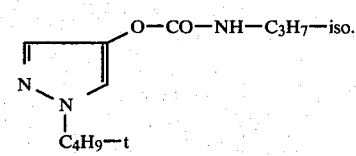

6. A compound according to claim 1, wherein such compound is 1-isopropyl-pyrazol-4-yl N-ethylcarbamate of the formula

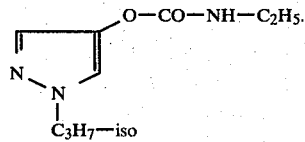

7. An insecticidal and nematicidal composition comprising an insecticidally and nematicidally effective amount of a compound according to claim 1 in admixture with a diluent.

8. A method for combating insects and nematodes comprising applying to the insects or nematodes, or to a hatibat thereof, an insecticidally or nematicidally effective amount of a compound according to claim 1.

9. The method according to claim 8, wherein such compound is
1-isopropyl-pyrazol-4-yl N-n-propylcarbamate,
1-tert.-butyl-pyrazol-4-yl N-ethylcarbamate,
1-tert.-butyl-pyrazol-4-yl N-isopropylcarbamate
or
1-isopropyl-pyrazol-4-yl N-ethylcarbamate.

* * * * *